(12) United States Patent
Kasprzak (10) Patent No.: US 8,123,796 B2
(45) Date of Patent: Feb. 28, 2012

(54) STENT PROSTHESIS FOR VASCULAR SURGERY IN PARTICULAR IN THE AREA OF THE AORTIC ARCH

(75) Inventor: Piotr Kasprzak, Regensburg (DE)

(73) Assignee: Piotr Kasprzak, Regensburg (DE)

( * ) Notice: Subject to any disclaimer, the term of this patent is extended or adjusted under 35 U.S.C. 154(b) by 484 days.

(21) Appl. No.: 11/816,605

(22) PCT Filed: Feb. 16, 2006

(86) PCT No.: PCT/DE2006/000285
§ 371 (c)(1),
(2), (4) Date: Aug. 17, 2007

(87) PCT Pub. No.: WO2006/086969
PCT Pub. Date: Aug. 24, 2006

(65) Prior Publication Data
US 2008/0167703 A1    Jul. 10, 2008

(30) Foreign Application Priority Data
Feb. 17, 2005   (DE) .......................... 10 2005 007 341

(51) Int. Cl.
*A61F 2/06* (2006.01)
(52) U.S. Cl. .................. 623/1.34; 623/903; 623/1.23
(58) Field of Classification Search .............. 623/1.11, 623/1.13, 1.15, 1.23, 903
See application file for complete search history.

(56) References Cited

U.S. PATENT DOCUMENTS

| | | | |
|---|---|---|---|
| 5,423,849 A * | 6/1995 | Engelson et al. | 606/191 |
| 5,690,644 A | 11/1997 | Yurek et al. | |
| 6,099,548 A * | 8/2000 | Taheri | 606/198 |
| 6,340,367 B1 | 1/2002 | Stinson et al. | |
| 6,723,116 B2 * | 4/2004 | Taheri | 623/1.11 |
| 2003/0135257 A1 | 7/2003 | Taheri | |
| 2006/0206202 A1 * | 9/2006 | Bonhoeffer et al. | 623/2.11 |
| 2007/0233223 A1 * | 10/2007 | Styrc | 623/1.11 |

FOREIGN PATENT DOCUMENTS

| | | |
|---|---|---|
| DE | 9321003 U1 | 9/1995 |
| WO | WO 94/15534 | 7/1994 |
| WO | WO 95/21592 | 8/1995 |
| WO | WO 02/070167 | 9/2002 |

OTHER PUBLICATIONS

PCT/DE2006/000285 Int'l Search Report from Counterpart WO Case, May 24, 2006, Kasprzak.
PCT/DE2006/000285 Translation of IPRP from Counterpart WO Case, Sep. 20, 2007, Kasprzak.

* cited by examiner

*Primary Examiner* — Brian Pellegrino
*Assistant Examiner* — Seema Swaminathan (57) ABSTRACT

A stent prosthesis for vascular surgery for inserting into an artery, particularly for bridging a vascular enlargement in the area of the aortic arch, comprising a tubular flexible and radially expandable stent body, on which at least one tear-proof long thread is attached in a fixed manner at a point of attachment on the outer peripheral surface of the stent body in the front portion thereof The thread can be recognized under x-ray radiation and has a free thread length of a number of decimeters and, starting from the point of attachment, is exposed outside the stent body so that the stent body, while following the thread, can be passed into the artery and can be placed, by means of the thread, in position inside the artery and can be subsequently fixed to the vascular wall.

9 Claims, 6 Drawing Sheets

STENT PROSTHESIS FOR VASCULAR SURGERY IN PARTICULAR IN THE AREA OF THE AORTIC ARCH

REFERENCE TO RELATED APPLICATIONS

This application is a 371 of PCT Patent Application Serial No. PCT/DE2006/000285, filed 16 Feb. 2006, which claims priority from German Patent Application No. 102005007341.7, filed 15 Feb. 2005, the disclosures of which are incorporated by reference herein in their entirety.

BACKGROUND

The present invention relates to a stent prosthesis for vascular surgery, in particular to a stent prosthesis for bridging a vascular enlargement in the area of the aortic arch, i.e. for example immediately at, close to, or at a certain distance to the aortic arch.

For many years, stents, also known as stent prostheses or stent implants, have been used in vascular surgery, radiology and heart surgery for eliminating aortic aneurysms. Such a stent prosthesis represents a tubular stent body comprising a sheathing made from a generally liquid-proof material, in particular synthetic material which is flexibly pliable and radially expandable. Such stent body is inserted through the artery and placed at the location of treatment in a radially folded state in an insertion tube, for example of a catheter, and is released by the catheter at the location of treatment so that the stent body is expanded or unfolded and attaches itself close to the vascular wall at least with its front end portion and rear end portion during insertion, in particular in front of and behind the vascular enlargement. In the sheathing wall of the stent body, a wire grating material or braided wire is generally provided, which radially expands due to its own elasticity, when the stent body is pushed out of the insertion tube of the catheter for the purpose of releasing the stent, or when the insertion tube is withdrawn for the purpose of releasing the stent, or when the stent body is expanded—for example by means of a balloon catheter.

The folded stent is for example inserted through a cut in the skin of the groin via the artery located underneath, placed in the aorta and is unfolded there in such a manner that the vascular enlargement or sac is entirely bypassed or eliminated. For this purpose it is necessary for the stent to be safely anchored before and after sacculation and for it to seal in such a manner that no more direct blood flow to the sac is possible. This is effected while the blood flows and during x-ray radiation, which makes an accurate alignment complicated.

A special difficulty exists in the area of the thoracic aorta, particularly in cases in which the arm supplying artery or the carotid artery is partially or completely covered where it branches off the aorta. Entirely blocked vital lateral rami also might have to be treated by means of a bypass procedure. A precondition, however, is that at least one of the main lateral arteries branching off the aortic arch (truncus brachio-cephalicus) remains open. It is even more difficult to position a lateral opening in the stent prosthesis, which needs to be placed very accurately, in front of the site where it branches off the lateral ramus (for example truncus brachio-cephalicus) so that blood flow in the respective artery is allowed. A blocking of this artery would cause severe complications. An accurate placing of the stent is further impeded by the curved course of the thoracic aorta at the aortic arch.

EP 0 894 481 A2 describes a long marker thread made from or with a material recognizable during x-ray treatment, attached alongside, for example, the plaited outer jacket of the stent body in such a manner that the place and position of the stent body may be detected under an x-ray radiation by means of the marker thread while inserting and placing the stent body in the artery. Such marker thread, the proximal thread end of which is for example fixed in the insertion catheter, is attached to the stent body in such a manner that it can be pulled out of the stent body after positioning the stent body. It is also possible that fixedly attached marker threads are provided, for example knotted ones, which permanently remain on the stent body and which do not significantly extend away from the stent body.

SUMMARY

The present invention creates a stent prosthesis which is equipped with a placing aid and/or fixing aid.

According to the present invention, at least one long thread, possibly two or more long threads is/are fixedly attached with one of its thread ends at an associated point of attachment located on the peripheral sheathing of the stent body on the outer peripheral surface thereof on or preferably at a distance to the front end (extending leading end the stent body during insertion). The thread material or material components contained therein or the coating of the thread is/are visible under x-ray radiation. The respective point of attachment may in particular be situated in the front half portion of the length of the stent body, for example in the front third or quarter portion of the length of the stent body. The thread length of the long thread, that, starting from the point of attachment, is exposed outside the stent body is by a length of at least ten centimeters, preferably several decimeters, sufficiently long to be passed with its free thread end, for example through a cut in the skin of the groin, prior to insertion of the stent, into the blood stream of the aorta, and may be caught in the artery and extracted from the artery through the point of puncture by means of an auxiliary puncture of the aorta from the throat or for example by means of an auxiliary puncture of a lateral ramus of the artery from another part of the body, with the aid of a special catheter or appliance (for example by means of a so-called lasso catheter).

This allows the stent, that is passed into the blood stream of the artery following the thread, to be accurately aligned and placed, by means of the thread, at the given point of attachment on the inner wall of the aorta, for which purpose the respective point of puncture is determined prior to the operation, in a given case by adjustment to the location of a lateral stent opening situated in the sheathing of the stent body as well as to the place where the thread is attached to the stent body. This also applies to stents including more than one prefabricated lateral stent opening. Furthermore, the stent, that, for example by fixing the stent with its front and rear stent ends to the vascular wall, may be additionally fixed to a third place by means of the thread. For this purpose, the thread or the threads may be anchored on the vascular wall in such a manner that such third fixation is permanent.

In accordance with the present invention, the long thread or threads are therefore designed to be sufficiently tear-proof for placing and/or fixing the stent body, and they are fixedly attached to the stent body in a tear-proof manner so that they cannot get detached from the stent body during manipulation of the stent body.

Instead of one single long thread which is attached at the point of attachment to the outer surface of the stent body, several long threads of the kind described in the present invention, in particular two threads attached to the same point of the outer surface, which are also referred to as double threads, or attached to different points of the outer surface, may be fixedly attached to the stent body. For example, two threads, one of which or both of which may be designed as single threads or double threads, may be fixedly attached at points of attachment located at the outer surface of the stent body at a distance from each other. In this manner the positioning of the stent may be corrected by means of the first and/or the second thread and the fixation of the stent body may be effected by means of the first and/or the second thread.

The respective point of attachment may be set in conformity with the anatomy of the patient prior to the operation so that the manufacturer may respectively prepare the stent. If several threads according to the present invention are attached at different typical points of the outer surface, those threads not to be used may be cut off immediately prior to the operation.

In case the stent body comprises a lateral opening for the purpose of keeping the portion clear where an artery branches off, the point of attachment of the thread or in particular double-thread is preferably located at a distance from the opening, at the side averted from the front end of the stent body. Such distance may amount to for example 1 to 3 cm or more, in adjustment to the chosen point of puncture. In addition, the point of attachment of the single or double-thread is preferably located on or near the same generatrix line on which the greatest diameter of the opening is situated. The places where the lateral opening and the point of attachment of the thread are located may equally be set in relation to each other prior to the operation. In addition, a long thread according to the present invention may be attached at the side of the opening facing the front end of the stent body. The thread may also be fixedly attached at another point of attachment, situated on the outer surface of the stent body between the front end, i.e. the distal end of the stent body, and the rear end, i.e. the proximal end of the stent body. In a given case the/a long thread according to the present invention may be attached at a point of attachment that is located directly at the front end or the rear end of the stent body.

A stent prosthesis in accordance with the present invention may also include a front or rear lateral opening in its stent body, that opens out externally into a hose-like sleeve portion that is sealingly attached at the sheathing of the stent body around the lateral opening. Such sleeve portion, by which the lateral opening is extended outwards, may serve the purpose of such sleeve portion being extended into a lateral artery which is to be kept free by the lateral opening of the stent body. With such embodiment, at least one long thread in accordance with the present invention may be fixedly attached at a respective point of attachment located at the free edge or on the outside of the sleeve portion, so that the sleeve portion may be drawn into the lateral artery by means of such thread, and, in a given case, may be fixed to the vascular wall therein. In this manner also several long threads may be attached to the sleeve portion.

With such embodiment it may be sufficient to provide the long thread(s) according to the present invention on the sleeve portion only. In this way the stent body in the current case generally may be placed and/or fixed at its point of attachment in the artery, by means of the thread(s) and with the aid of the sleeve portion. With such embodiment, alternatively, at least one additional long thread may be attached to the sheathing coat of the stent body.

The configuration of the stent body including one or several threads on the side averted from the lateral opening, in accordance with the present invention, is particularly advantageous, since the thread allows an accurate placing of the lateral opening, which may be further enhanced by the use of an additional thread located at the front side of the opening.

If wanted, an additional lateral opening my be provided in the sheathing of the stent body for the purpose of checking the correct positioning of the stent after a partial unfolding and prior to the final release, such additional opening being offset against the opening along the circumference of the stent body, and such opening may be axially offset against the first opening also in relation to the rear end of the stent body. Such opening may be used to insert a monitoring catheter from the outside to the inside (into the stent body) and subsequently back from the inside to the outside, for monitoring purposes, via the first opening into the lateral artery to be supplied, e.g. into the truncus brachio-cephalicus. If wanted, an additional fixation of the stent opening in the lateral artery may be effected via the first opening by means of an additional stent. The additional lateral opening is then sealed at the end of the operation, e.g. by means of an additional stent.

The present invention furthermore suggests a catheter for inserting the stent in accordance with the present invention, in which at least one preferably axial slit is situated in the free end portion of the insertion tube, such slit penetrating the jacket thereof and extending up to the frontal end thereof; through such slit, the respective thread can be led out of the catheter before the folded stent is released from the catheter.

The slit allows that the stent can be placed, by means of the introduced thread, yet prior to its emergence from the free end portion of the insertion tube of the catheter and thus prior to the unfolding of the stent, into the intended location and kept in such location, without allowing a displacement of the stent while the same is released.

BRIEF DESCRIPTION OF DRAWINGS

The present invention is illustrated by means of preferred embodiments, which are evident in the drawings. The drawing shows.

DETAILED DESCRIPTION

Figure 1:
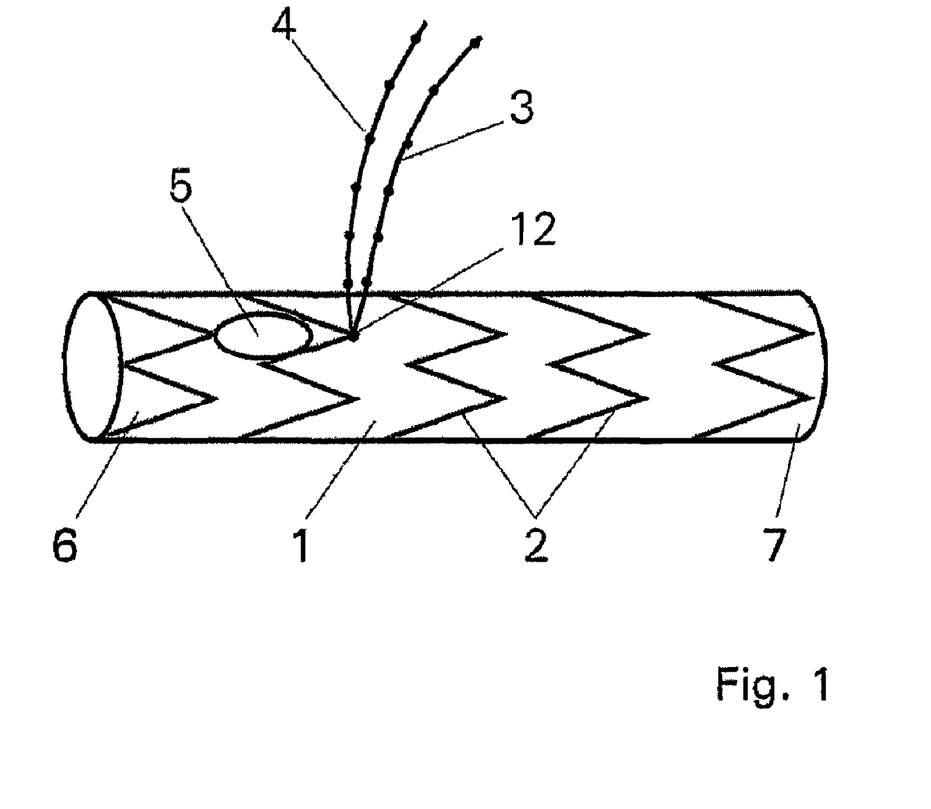
FIG. 1 a stent prosthesis including an opening and two threads attached at the stent body.

As can be seen from FIG. 1, a lateral opening 5 is provided on the tubular stent body 1 on the front quarter portion of the length of the stent body at a distance from the front end 6 thereof. In the tubular stent body 1, on or in the peripheral sheathing thereof, that is liquid-proof with regard to blood with the exception in openings provided, a wire grid, wire fabric or braided wire 2 is arranged. At a short distance behind the opening 5, offset from the rear end 7 of the stent body, two long threads 3, 4 according to the present invention are attached as double-threads. A metal wire or metal particles or the like are integrated into the threads, so that the threads are visible under x-ray radiation during an operation. The thread (s) may alternatively be provided with a coating made from material visible in x-ray radiation, so that the thread material as such does not need to be visible under x-ray radiation.

Figures 2, 3, 4:
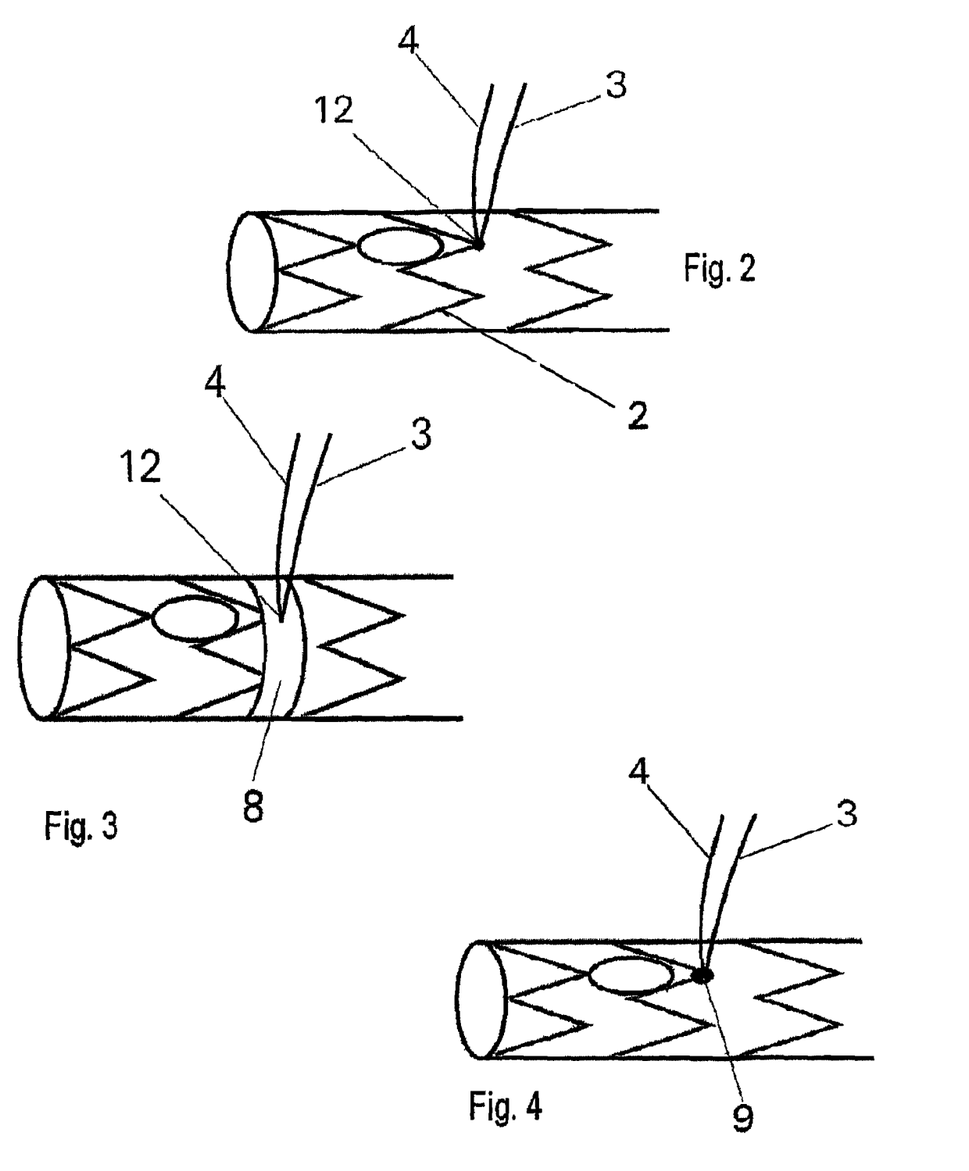
FIGS. 2-4 different variations of a thread fixation at the stent.
Figure 5:
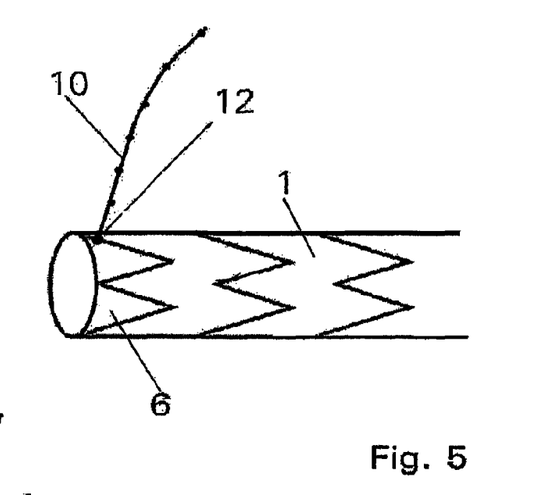
FIGS. 5-8 examples of different thread attachments.
Figure 6:
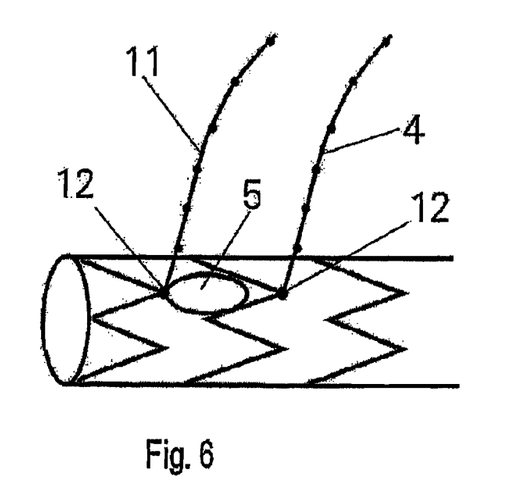
Figure 7:
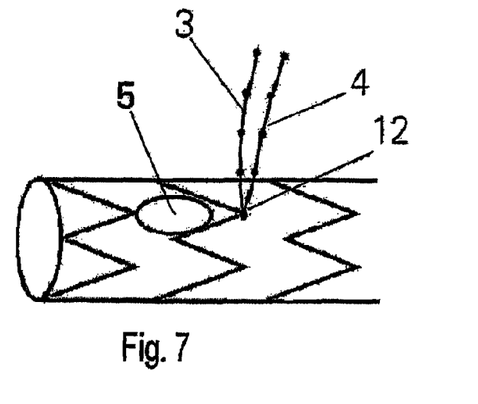

Threads 3, 4 may be attached at their point of attachment 12, that is situated on the outer surface of the stent body, to the stent body e.g. in the metal grit 2 (FIG. 2) on a reinforcing tape 8 (FIG. 3) provided around the stent body, on a patch 9 (FIG. 4) or in a similar manner in such a way that they may not tear-out during insertion and while placing the stent, as well as after the operation.

Figure 8:
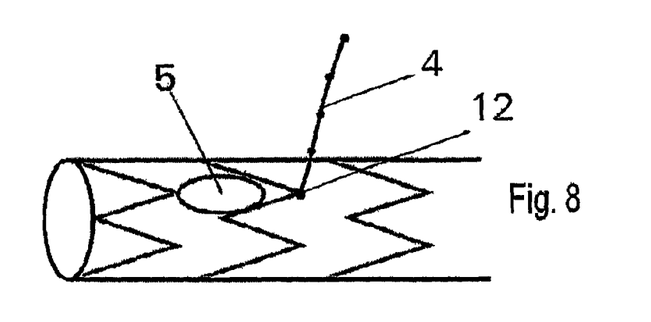

From FIGS. 5 to 8, further exemplary applications of the present invention can be seen as a stent without any opening, but including thread 10 provided on the front end 6 of the stent body 4 in accordance with the present invention (FIG. 5), as a stent including opening 5 and thread 11 located in front of opening 5 (FIG. 6), as a stent including two threads 3, 4 provided as a double-thread behind opening 5, as in FIG. 1, or as a stent including a single thread 4 behind opening 5 (FIG. 8).

Figure 9:
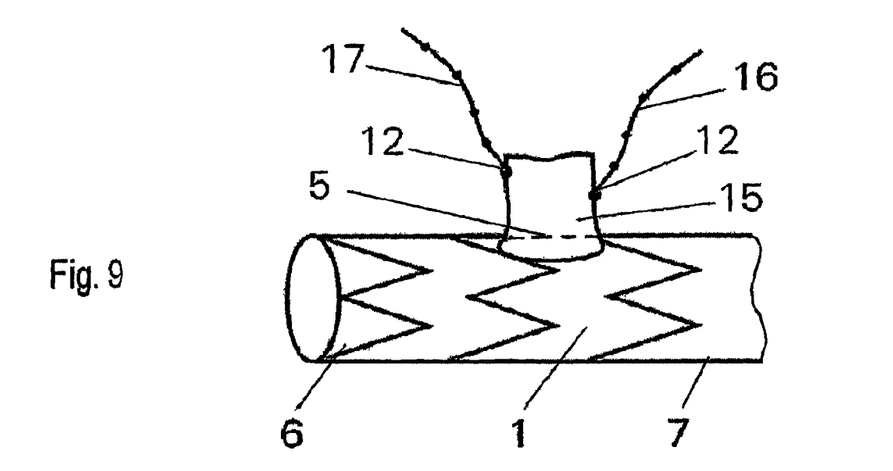
FIG. 9 an example of a stent prosthesis in accordance with the present invention including a lateral sleeve portion.

FIG. 9 shows an example of a stent body 1 according to the present invention, comprising a sleeve portion 15 around its lateral opening 5, which is to be extended into a lateral ramus of the artery. For this purpose two long threads 16, 17 are attached at diametrically opposite points of attachment 12 on the outside of the sleeve portion. At least one additional long thread may be provided at a suitable point of attachment on the outer peripheral surface of the stent body (not shown).

Figure 11:
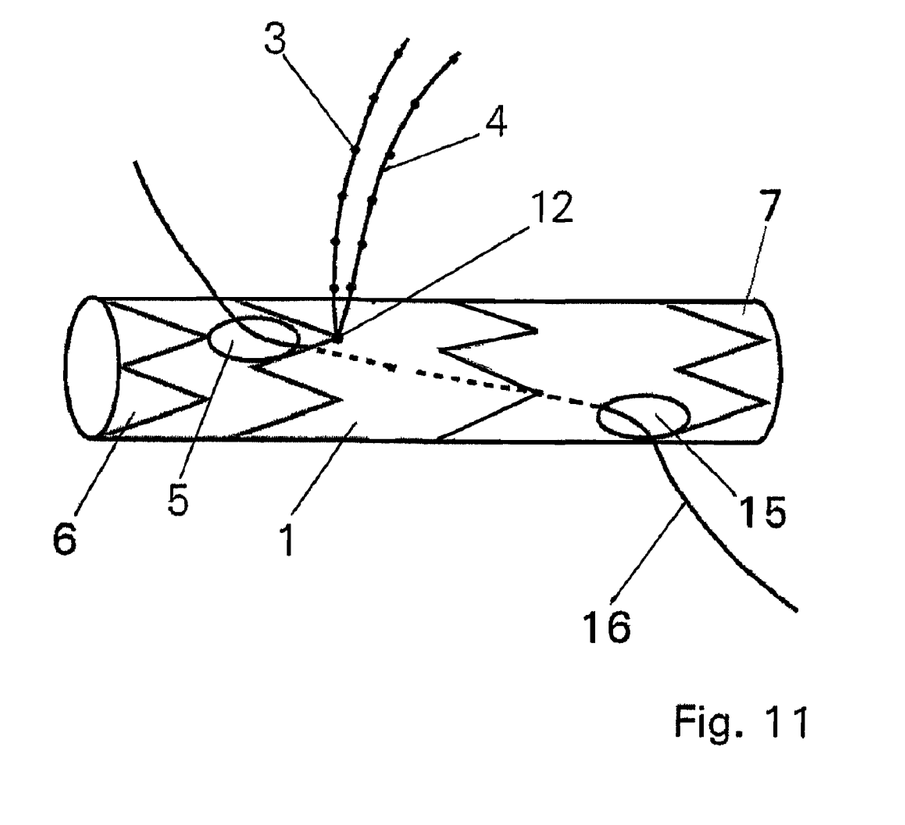
FIG. 11 a stent including a second opening.

As can be seen in FIG. 11, an additional lateral opening 15 may be provided in the sheathing of the stent body 1, e.g. axially at a distance from the opening 5 in the direction of the rear end of the stent body 1 and offset against opening 5 along the periphery of the stent body for example by an angular degree of about 45 degrees or more. Additional opening 15 provides another opportunity for monitoring the insertion of the monitoring catheter 16 via openings 15 and 5 and, if necessary, the insertion of another stent (not shown) via inserting catheter 16 for fixing opening 5 in the adjacent lateral artery.

Figure 10:
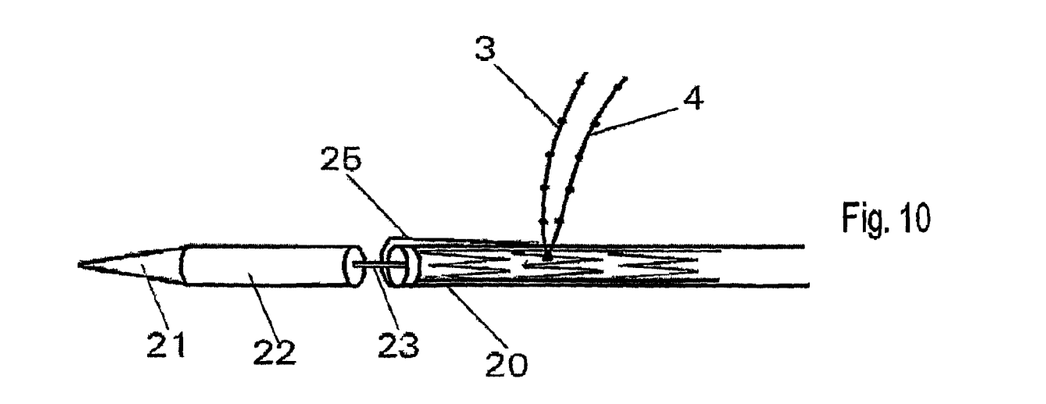
FIG. 10 an example of an insertion catheter including a slit and an outer cover.

FIG. 10 shows the distal end of a catheter insertion tube 20 including a foldedly arranged stent in accordance with the present invention (not shown). At the free end portion of the insertion tube 20 at least one axial slit 25 is provided, penetrating its tube material and extending to its frontal end, through which slit thread 3 or 4, as applicable, may be led out of the catheter before the folded stent is released.

The tip of the catheter attached to catheter wire 23 comprises a cover 22, proximally sticking out from the same, such cover may be pushed over the free end of the insertion tube 20 to threads 3, 4, emerging laterally, in order to hold the slit catheter portion together and hence the stent therein, and such cover may be pushed away from the end portion of the insertion tube 20 my means of the catheter wire 23, prior to the withdrawal of the insertion tube 20.

Figure 12:
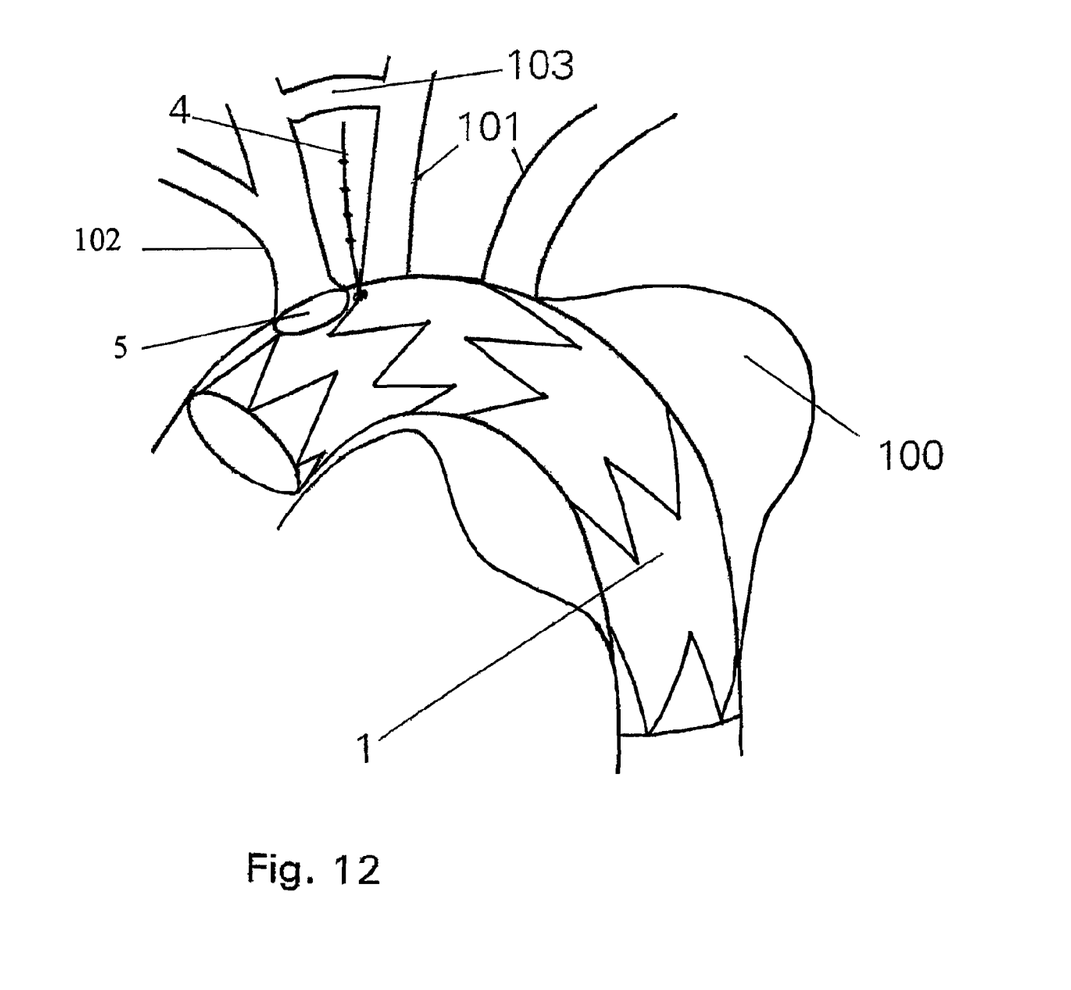
FIG. 12 an exemplary application for inserting a stent into the aorta

FIG. 12 shows a drawing of an exemplary application for inserting the stent body 1 into the aorta arch for bridging a sac 100 in accordance with the present invention. The stent body is sufficiently flexibly bendable so that it may follow the curve of the aortic arch. The truncus brachio-cephalicus 102 is kept free by the lateral opening 5 of the stent body, whereas the other two arteries 101 branching off are blocked by the stent body; their blood supply is provided for by bypass 103. By means of the long thread 4 attached to the stent body 1 in accordance with the present invention, the stent body 1 may be placed and subsequently fixed in its position.

The invention claimed is:

1. A stent prosthesis for vascular surgery for inserting into an artery to bridge and by-pass a vascular enlargement of the artery, comprising a tubular flexible and radially expandable stent body having a front end and a rear end that is spaced from the front end by a tube length, the stent body including along said tube length a tubular peripheral liquid-proof sheathing that is liquid-proof against liquid blood along said tube length and has a peripheral outer surface along said tube length, the tubular sheathing configured to be radially expandable with respect to a longitudinal axis of the tubular sheathing from a radially folded condition to an unfolded condition during said insertion into the artery to open an inside channel longitudinally through the sheathing and to sealingly attach itself around an inner wall of the artery in front of and behind the vascular enlargement in the artery to bridge the vascular enlargement in the artery by the liquid-proof tubular sheathing and bypass the vascular enlargement through said inside channel, the stent prosthesis further comprising at least one tear-proof long thread, the tear-proof thread including a fixed end and a free end, wherein the fixed end is permanently and fixedly attached to the sheathing in a tear-proof manner at a point of attachment located directly on the outer surface of the sheathing in a distance from the front end and from the rear end of the stent body, the long thread including a material that is visible in x-ray radiation and having a free thread length that extends from the fixed end of the long thread up to the free end thereof, wherein the free thread length includes the free end and is freely exposed outside the stent body, and the free thread length of the long thread is of several decimeters configured to be passed with the free end of the thread as a leading end into the artery in advance of passing the stent body into the artery and further configured to be caught in the artery by a surgical appliance and extracted out from the artery by the surgical appliance through an auxiliary puncture of a vascular wall, the long thread further configured to resist pulling forces applied onto the free thread length for manipulation of the implanted stent body to be aligned and placed in position in the artery and for a subsequent fixation of the stent body to the vascular wall by means of the extracted free thread length, wherein the fixed end of the long thread is fixedly attached to the sheathing in such a tear-proof manner that the fixed end cannot get detached from the stent body by applying said pulling forces onto the free thread length.

2. A stent prosthesis as claimed in claim 1, wherein the long thread is a double-thread.

3. A stent prosthesis as claimed in claim 1, wherein a first lateral opening is provided through the peripheral sheathing of the stent body into the inside channel, the first lateral opening configured to keep a portion of the stent body, when inserted into the artery, at a location of the artery clear where a side artery branches off, and the point of attachment of the long thread is located on the peripheral sheathing in a short distance from the lateral opening.

4. A stent prosthesis as claimed in claim 3, wherein the point of attachment of the long thread is located on the peripheral sheathing of the stent body on that side of the first lateral opening that is averted from the front end of the stent body.

5. A stent prosthesis as claimed in claim 4, wherein said at least one tear-proof long thread includes a second tear-proof long thread that is permanently and fixedly attached in said tear proof manner at the peripheral sheathing at a second point of attachment at that side of the first lateral opening that faces the front end of the peripheral sheathing of the stent body.

6. A stent prosthesis as claimed in claim 1, wherein a lateral opening is provided through the peripheral sheathing of the stent body into the inside channel, the first lateral opening configured to keep a portion of the stent body, when inserted into the artery, at a location of the artery clear where a side artery branches off, and the peripheral sheathing includes a sleeve portion configured to extend the lateral opening outside of the peripheral outer surface of the sheathing, wherein the point of attachment of the long thread is arranged on the sleeve portion.

7. A stent prosthesis as claimed in claim 3, wherein a second lateral opening is formed through the peripheral sheathing into the inside channel, the second lateral opening configured to allow insertion of a monitoring catheter through the second lateral opening into the inside channel, wherein the second lateral opening is offset from the first lateral opening in the circumferential direction of the peripheral sheathing and offset from the first opening in an axial direction towards the rear end of the stent body.

8. A vascular surgery method for implanting a stent prosthesis at an application site in an artery by inserting the stent prosthesis into and through the artery to bridge and by-pass a vascular enlargement of the artery, wherein the stent prosthesis comprises a tubular flexible and radially expandable stent body having a front end and a rear end that is spaced from the front end by a tube length, and including along said tube length a tubular peripheral liquid-proof sheathing that is liquid-proof against liquid blood along said tube length and that has an outer peripheral surface along said tube length, the sheathing configured to be radially expandable with respect to a longitudinal axis of the tubular sheathing from a radially folded condition to an unfolded condition during said insertion into the artery to open an inside channel longitudinally through the sheathing and to sealingly attach itself around an inner wall of the artery in front and behind the vascular enlargement in the artery to bridge the vascular enlargement by the liquid-proof sheathing and bypass the vascular enlargement through said inside channel, the method comprising:

permanently fixing at least one tear-proof long thread with an end thereof to the outer peripheral surface of the sheathing in a tear-proof manner at a point of attachment located directly on the outer surface of the sheathing in a distance from the front end and from the rear end of the stent body, the long thread including a material that is visible in x-ray radiation and having a free thread length of several decimeters that extends from the fixed end of the long thread up to a free end of the long thread and includes the free end and that is freely exposed outside the outer peripheral surface of the sheathing, inserting the stent prosthesis into the artery by passing the free end of the free thread length of the at least one long thread and subsequently the free thread length into streaming blood in the artery in advance of the stent body and passing the stent body into the artery subsequently to the free thread length, catching the free thread length in the artery by a surgical appliance in a region of the application site and subsequently extracting the free thread length by the surgical appliance from the artery through an auxiliary puncture of a vascular wall, and manipulating the stent body in the artery by pulling on the extracted free thread length of the long thread during passing of the stent body into the artery in such a manner that the stent body is placed and aligned in the artery at the application site into a predetermined position, followed by fixing the extracted free thread length to the vascular wall after the stent body is fixed in the predetermined position.

9. A stent prosthesis as claimed in claim 1, wherein said at least one tear-proof long thread includes a plurality of tear-proof long threads separately attached in a tear-proof manner at different points of attachment of the peripheral outer surface of the sheathing.

* * * * *